United States Patent
Erlandsson et al.

(10) Patent No.: US 9,304,096 B2
(45) Date of Patent: Apr. 5, 2016

(54) METHOD OF MEASURING A CAPACITANCE

(75) Inventors: Dag Erlandsson, Rostanga (SE); Martin Hedstrom, Jonstorp (SE); Bo Mattiasson, Hjaerup (SE); Joakim Larsson, Morarp (SE)

(73) Assignee: CAPSENZE HB, Billeberga (SE)

(*) Notice: Subject to any disclaimer, the term of this patent is extended or adjusted under 35 U.S.C. 154(b) by 528 days.

(21) Appl. No.: 13/882,641

(22) PCT Filed: Oct. 31, 2011

(86) PCT No.: PCT/SE2011/000192
§ 371 (c)(1),
(2), (4) Date: Jul. 24, 2013

(87) PCT Pub. No.: WO2012/060758
PCT Pub. Date: May 10, 2012

(65) Prior Publication Data
US 2013/0304397 A1    Nov. 14, 2013

(30) Foreign Application Priority Data
Nov. 1, 2010  (SE) ..................................... 1051143

(51) Int. Cl.
*G01R 29/26* (2006.01)
*G01N 27/22* (2006.01)
*G01N 27/327* (2006.01)
*G01R 27/26* (2006.01)

(52) U.S. Cl.
CPC ............ *G01N 27/22* (2013.01); *G01N 27/3276* (2013.01); *G01R 27/2605* (2013.01); *G01N 27/228* (2013.01); *G01R 27/26* (2013.01)

(58) Field of Classification Search
USPC .............................................. 702/19, 22, 30
See application file for complete search history.

(56) References Cited

U.S. PATENT DOCUMENTS

| 4,147,050 A | 4/1979 | Rubel et al. |
| 4,458,196 A | 7/1984 | Goyal et al. |
| 4,795,966 A | 1/1989 | Cook |

(Continued)

FOREIGN PATENT DOCUMENTS

| JP | 2003240506 | 8/2003 |
| WO | 9914596 | 3/1999 |

OTHER PUBLICATIONS

International Search Report for PCT/SE2011/000192, Completed by the Swedish Patent Office on Jan. 13, 2012, 5 Pages.

(Continued)

*Primary Examiner* — Huan Tran
(74) *Attorney, Agent, or Firm* — Brooks Kushman P.C.

(57) ABSTRACT

A method of measuring a capacitance (C) of a sensor having a working electrode that is coated by an insulating layer and a ligand forming an affinity surface. The method involves the steps of bringing the electrode into contact with an analyte, supplying a constant first current ($I_1$), and a constant second current ($I_2$) of opposite direction to the first current ($I_1$), and a constant third current ($I_3$) of same direction as the first current ($I_1$) during determined time periods to the sensor. Further the method includes sampling the potential (V) built up across the sensor, and calculating the capacitance of the sensor from the inclination (B, D, F, H) of a potential curve received in response to the current supply. A method used for detection of an interaction between a ligand and an analyte is also disclosed.

15 Claims, 3 Drawing Sheets

(56) References Cited

U.S. PATENT DOCUMENTS

| | | |
|---|---|---|
| 5,585,733 A | 12/1996 | Paglione |
| 6,356,086 B1 | 3/2002 | Cook et al. |
| 6,436,699 B1 * | 8/2002 | Berggren et al. .......... 435/287.2 |
| 2005/0104604 A1 | 5/2005 | Mellert et al. |
| 2005/0196877 A1 | 9/2005 | Weinberg et al. |
| 2005/0270042 A1 | 12/2005 | Doljack |
| 2007/0151848 A1 | 7/2007 | Novak et al. |
| 2007/0154951 A1 | 7/2007 | Kermani |

OTHER PUBLICATIONS

Wongkittisuksa et al. Biosensors and Bioelectronics 2011, vol. 26, p. 2466-2472, "Development and application of a real-time capacitive sensor."

Loyprasert et al. Biosensors and Bioelectronics 2010, vol. 25, p. 1977-1983, "Sub-attomolar detection of cholera toxin using a label-free capacitive immunosensor."

* cited by examiner

METHOD OF MEASURING A CAPACITANCE

CROSS-REFERENCE TO RELATED APPLICATION

This application is the U.S. national phase of PCT Application. No. PCT/SE2011/000192 filed Oct. 31, 2011, which claims priority to Swedish Patent Application No. 1051143-4, filed on Nov. 1, 2010, the disclosures of which are incorporated in their entirety by reference herein.

FIELD OF INVENTION

The present invention relates to a method of measuring a capacitance of a sensor.

Further, the invention relates to a use of a method for detection of an interaction between a ligand and an analyte.

BACKGROUND OF THE INVENTION

Different techniques for the analysis of biomolecules are available on the market today. Conventional quantitative methods are still in use, as for example mass spectrometry, NMR or chromatography. A demand for more sensitive methods has resulted in development of technologies using biosensors, the most frequent are gravimetric and optical methods. However, the most sensitive way for analysing biomolecules by use of a biosensor is performed by electrochemical technology, which is based on a combination of biological molecules and electrodes.

Affinity sensors, for example immunosensors, are based on binding events between immobilized biomolecules (a ligand) and target molecules of interest (an analyte). The immobilization of the biomolecules is of vital importance for the ability to detect the binding events or interaction between the ligand and the analyte. The sensitivity obtained depends on the measuring principle of the sensor technique and the affinity properties and density of the ligand directed to the analyte.

An advantage with methods involving some affinity biosensors is that they can directly detect an interaction between an analyte in a solution and a ligand arranged at the surface of the sensor without the need of any labelled reagent, thus making the analysis less complicated and labour intense for the operator compared with competitive assays.

An affinity sensor can be used in different applications, e.g. for detecting biological contaminants, such as bacteria, viruses or toxic material thereof in tap water or in streams, or for detecting a chemical compound or a biological molecule, such as a protein or nucleic acid sequence.

In an electrochemical way, the concentration of an analyte in a solution can be calculated by measuring changes in dielectric properties, when the analyte interacts with the ligand arranged on the affinity surface of the biosensor electrode. For example, capacitive measurements or impedance measurements have been investigated for detecting different analytes.

A capacitive biosensor can be constructed by arranging capturing biomolecules (the ligand) in a thin layer on a working electrode, which previously has been coated by a thin insulating layer. The electrode is typically made of a noble metal, e.g. gold, but may also be made from other conducting materials. Then, the working electrode is arranged in a flow cell and is subjected to a potential pulse. At injection of the analyte into the flow cell, a complex of ligand-analyte is formed on the surface of the electrode due to the interaction between the analyte and the ligand, which will change the dielectric properties of the biosensor, for example the capacitance of the sensor will decrease. Hence, the analyte concentration of the solution can be evaluated by periodic measurements, before and after injection of the analyte, via measurement of the capacitance change.

WO 99/14596 describes a capacity affinity sensor based on an assembled monolayer on an electrode with immobilized recognition elements that are available to the analyte in a surrounding solution. The electrode is selective to those molecules in the solution that show affinity to the recognition elements on the surface.

A label-free immunosensor for the direct detection of cholera toxin (CT) is described in the article "Sub-attomolar detection of cholera toxin using a label-free capacitive immunosensor", in the paper Biosensors and Bioelectronics 25 (2010) 1977-1983. In this study the concentration of CT was determined by potentiostatic capacitance measurement, i.e. by detecting the change in capacitance caused by the formation of antibody-antigen complexes. This technique is based on the electrical double-layer theory for measuring changes in dielectric properties when an antibody-antigen complex is formed on a transducer surface. The capacitance measurement was determined from the current response obtained when a potentiostatic step of +50 mV was applied to the working electrode.

However, known methods using biosensors for measurement of changes in dielectric properties present several weaknesses.

Conventional capacitive measuring devices, as disclosed in the prior art, are sensitive for external electronic disturbances, such as background noise, which will affect the variability, and thus the accuracy of the measurement.

A drawback is that the working electrode has to be exchanged for a new one, when one or more measuring series have lapsed, due to the sharp potential input commonly used. This potential input will also affect the sensitive layer of biomolecules (biorecognition layer) and the affinity of the sensor in such way that the ligand may be partly denatured. The working electrode is finally worn out and has to be exchanged, resulting in a time-consuming operation.

Hence, one disadvantage is that several of the initial capacitance measurements in a measuring series have to be used for calibrating the electrode. This calibrating operation contributes to decrease the amount of relevant unknown samples that can be run on one sensor electrode before it needs to be replaced.

A critical step in designing capacitive biosensors is the immobilization of the layer of biorecognition elements on the electrode. If it is not sufficiently insulated, ions can move through the layer, causing short-circuiting of the system, leading to a decrease in signal or absence of signal. Interferences from redox couples in the electrolyte solution can also cause high Faradic background currents, and might increase the resistance current and decrease the capacitance response.

It is desirable to have an improved method for measuring capacitive changes when using a biosensor, and a more stable system for measuring a capacitance of a biosensor to increase the sensitivity and accuracy of the method.

SUMMARY OF THE INVENTION

An object of the present invention is to mitigate or eliminate one or more deficiencies and disadvantages of the prior art, singly or in any combination.

In a first aspect, the invention relates to a method of measuring the capacitance of a sensor having a capacitance and a resistance. The sensor has a working electrode that is coated by an insulating layer having a ligand arranged thereto, which form an affinity surface on said electrode. When an analyte is brought into contact with the ligand and couples thereto, the dielectric properties of the sensor will change. The capacitance is calculated from a potential curve received by potentials built up across the sensor in response to supply of constant currents.

The method comprises the steps of:

bringing said electrode into contact with an analyte;

supplying a constant first current to said sensor during a first time period by means of a current source until a potential built up across the sensor has reached a predetermined value and, simultaneously sampling the potential built up across the sensor;

supplying a constant second current to the sensor during a second time period by means of the current source, the second current having an opposite direction compared to the first current and having a same absolute value as the first current, wherein the second time period is equal to said first time period or is equal to said first time period multiplied with a factor two, and simultaneously sampling the potential built up across the sensor;

supplying a constant third current to the sensor during a third time period by means of the current source, the third current having the same direction as the first current and having the same absolute value as the first current, wherein if said second time period is equal to said first time period, the third time period is zero, and if said second time period is equal to said first time period multiplied with a factor two, the third time period is equal to said first time period; and calculating the capacitance of the sensor by means of an inclination of a potential curve received by the potential built up across the sensor in response to the supply of the constant currents, if said potential has returned to zero when a cycle including said time periods has lapsed.

The sampling is performed a plurality of times during each time period of current supply, such as about 100-1000 times per period.

In one embodiment, the capacitance of the sensor is calculated from inclinations of the potential curve received in response to the supply of the constant currents. During a single cycle of current supplies, several values of said capacitance are calculated. The capacitance is discarded if the potential built up across the sensor does not return to zero, when the third time period has lapsed. Also, if the capacitance calculated from said inclinations varies during a single cycle, the capacitance is discarded. In another embodiment, at least one inclination of said potential curve is used for determining error conditions.

The resistance of the sensor may be used as a control function, for controlling the stability of the method and the accuracy of the measuring values received. The resistance is determined from the vertical parts of said potential curve, and if said resistance is altered after consecutive supplies of the constant currents during a cycle the corresponding value of the capacitance is discarded.

Also, the resistance is used for identification of the electrode.

In a second aspect, the invention relates to a use of a method of measuring the capacitance for detection and quantification of an interaction between a ligand and an analyte. The alteration in capacitance of a sensor is used for determining the interaction between the ligand and the analyte.

In one embodiment the ligand can be an antibody and the analyte can be an antigen, or vice versa.

Also, use of the method may be applied for detecting an interaction between an analyte and a ligand, wherein the ligand and the analyte form an affinity pair of any of a couple selected from the list:

antibody—antigen lectin—glycoconjugate or carbohydrate alone protein with selective binding to other proteins, e.g. protein A and immunoglobulin G receptor—receptor binding entity nucleic acid—nucleic acid with complementary base sequence enzyme—enzyme inhibitor peptide from phage library and its target molecule any biomolecule and its either natural or synthetic binding ligand Further objects, features and advantages of the present invention will appear from the following detailed description, from the attached drawings and from the dependent claims.

BRIEF DESCRIPTION OF THE DRAWINGS

In order to explain the invention, embodiments of the invention will be described below with reference to the drawings, in which.

Same reference numerals have been used to indicate the same parts in the figures to increase the readability of the description and for the sake of clarity.

DETAILED DESCRIPTION OF EMBODIMENTS OF THE INVENTION

Below, embodiments of the invention will be described. These embodiments are described in illustrating purpose in order to enable a person skilled in the art to carry out the invention and to disclose the best mode. However, the embodiments do not limit the invention. Moreover, other combinations of the different features are possible within the scope of the invention.

Figure 1:
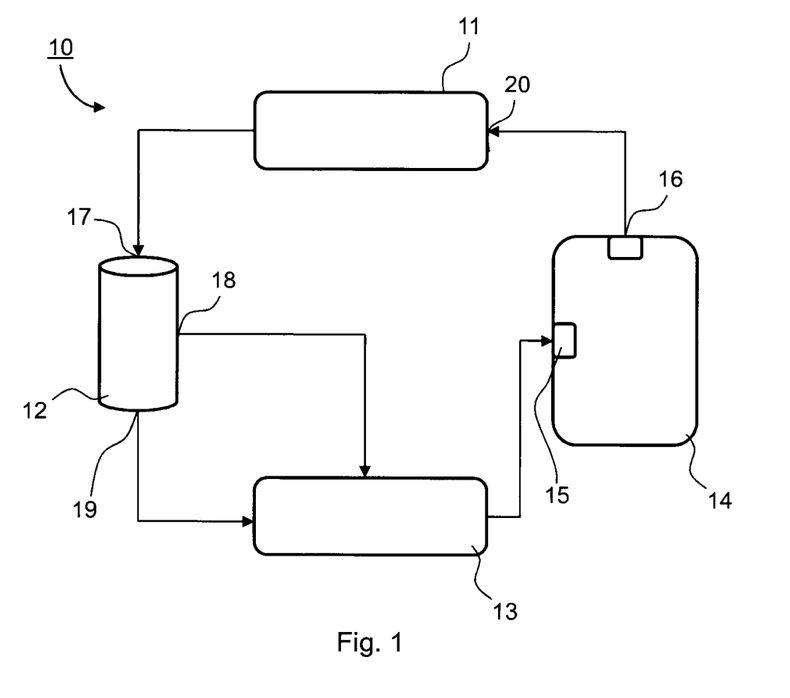
FIG. 1 is a schematic view of a system, which can be used for performing the method of measuring a capacitance according to the invention.

FIG. 1 shows a schematic view of a system 10, which can be used for performing a method of measuring a capacitance according to the invention. The system 10 comprises a current source 11, a flow cell 12, a potential differential amplifier 13, a processor 14, an analogue/digital (A/D) converter 15 and a digital/analogue (D/A) converter 16.

A first connector 17, a second connector 18 and a third connector 19 are arranged to the flow cell 12.

Figure 2:
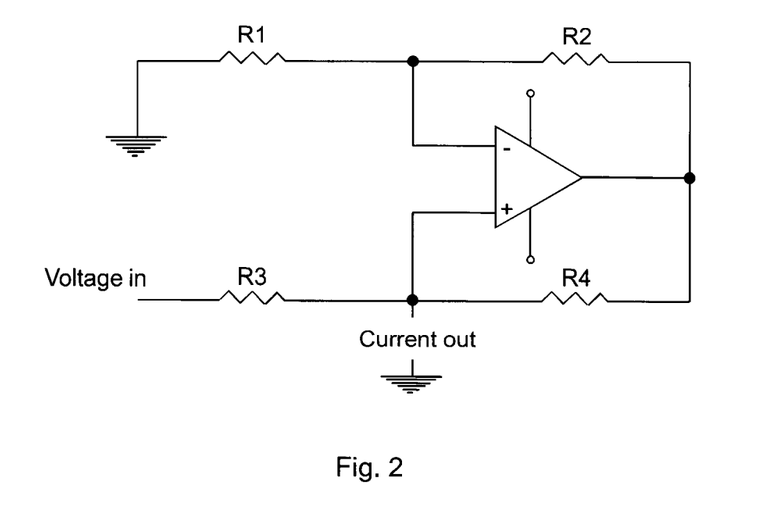
FIG. 2 is a schematic view of a Howland current pump of the system in FIG. 1.

FIG. 2 shows a current source 11, which delivers a constant current I to the flow cell 12 by the first connector 17. The value of the current is for example about a few microamperes (μA). The current I can be either positive or negative. If $V_{in}$ has a higher value than a reference potential $V_{ref}$, then $I_{out}$ is positive, and if $V_{in}$ has a lower value than $V_{ref}$, then $I_{out}$ is negative.

$I_{out}$ is zero when $V_{in}$ is equal to $V_{ref}$. In FIG. 2, the reference potential $V_{ref}$ is ground: when $V_{in}$ is positive, then $I_{out}$ is positive, and if $V_{in}$ is negative, then $I_{out}$ is negative. The negative and the positive values of the current I will be utilized as opposite directions of currents, which will be explained below. The current source 11 is for example a Howland current pump, which is described more precise by Robert A. Pease in National Semiconductor Application Note 1515 of Jan. 29, 2008.

The potential differential amplifier 13 is connected to the flow cell 12 by the second connector 18 and the third connector 19, which are arranged for measurement of a potential V across the flow cell 12, which is built up when a current is supplied.

The connector 17 for current supply is separated from the connectors 18 and 19 for avoiding influences from terminal resistances. Thus, the system 10 maintains constant impedance from the flow cell 12 to the different potential amplifier 13, which increases the stability of the system.

The differential amplifier 13 is connected to the processor 14 via the A/D converter 15 for converting the analogue potential V, built up across the flow cell 12, to a digital signal. The processor 14 may be embedded, and has software for digital computer capability. A display (not shown) is provided for presenting measuring data. The processor 14 is arranged to deliver a control potential U as an analogue output by the D/A converter to a control terminal 15 of the current source 11.

A working electrode is arranged within the flow cell 12. The volume of the flow cell 12 is arbitrary, for example 10 µl. The working electrode is made of a noble metal, such as gold, or made from other conducting materials, and is coated by an insulating layer that couples a layer of biomolecules (ligand) thereto. The insulating layer and the covalently attached biomolecules, hereinafter called the substrate, are forming an affinity surface on the working electrode. The insulating layer with the ligand arranged thereto is forming a dielectric layer having a thickness on the electrode. The manufacturing of the working electrode is known per se.

The system 10 has an auxiliary electrode, e.g. made of platinum wire, and at least one reference electrode, e.g. made of platinum wire, silver/silver chloride or a combination of platinum wire and silver/silver chloride, not shown.

Figure 3:
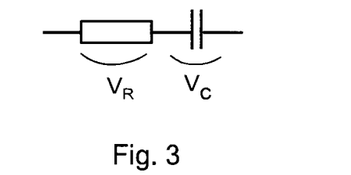
FIG. 3 shows schematically the potential components of a sensor of the system in FIG. 1.

The flow cell 12 contains a solution, i.e. an electrolyte, and forms a capacitive sensor having a resistance (R) 31 and a capacitance (C) 32 connected in series, as illustrated in FIG. 3 as a RC-circuit.

R 31 is the resistance between the gold electrode coated by the substrate and the complex of ligand-analyte, formed on the substrate, and the solution carrying the analyte. C is regarded as the total capacitance of the sensor, i.e. the capacitance of the flow cell 12, excluded the ideal ones.

At injection of an analyte into the flow cell 12, a complex of ligand-analyte is formed on the electrode surface due to the interaction between the molecules of the ligand and the analyte, when a constant current is supplied to the cell 12. The complex of ligand-analyte will make the affinity surface on the working electrode thicker, which will increase the thickness of the dielectric layer, leading to changes of the dielectric properties.

After the injection, the capacitance of the sensor will decrease, when the thickness of the affinity surface increases caused by said interaction, which is proportional to the concentration of the analyte injected. Hence, the amount of analyte injected can be calculated as the change in capacitance before and after injection.

Figure 4:
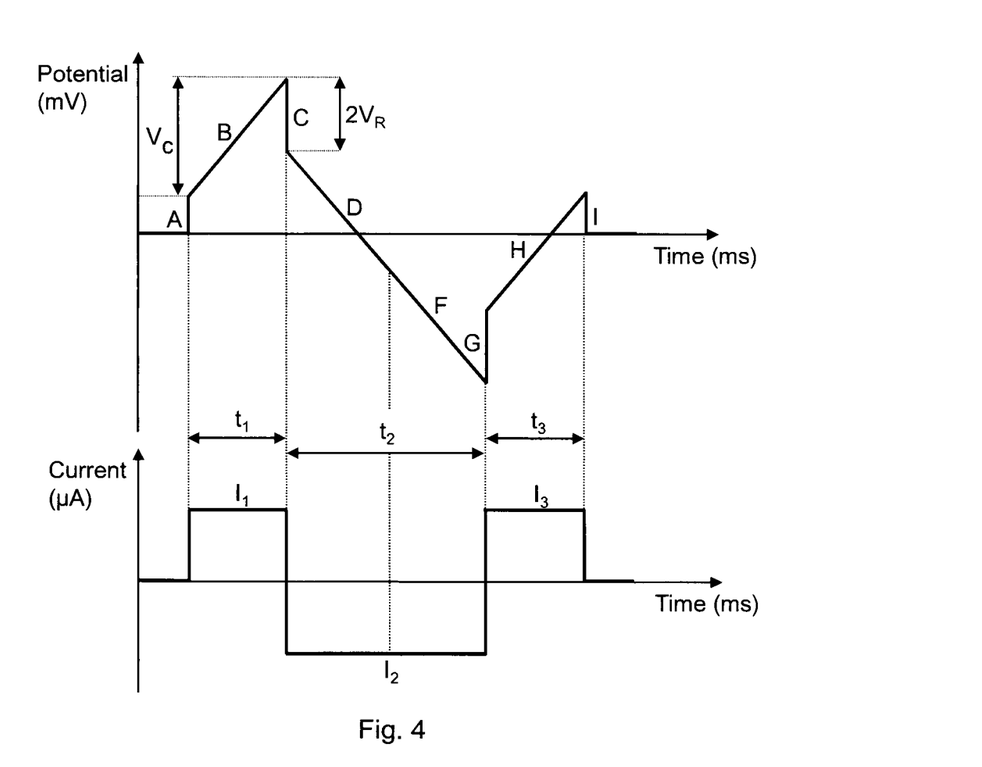
FIG. 4 shows a potential curve received in response to supply of constant currents during determined time periods to the sensor of the system in FIG. 1 according to a first embodiment of the method.
Figure 5:
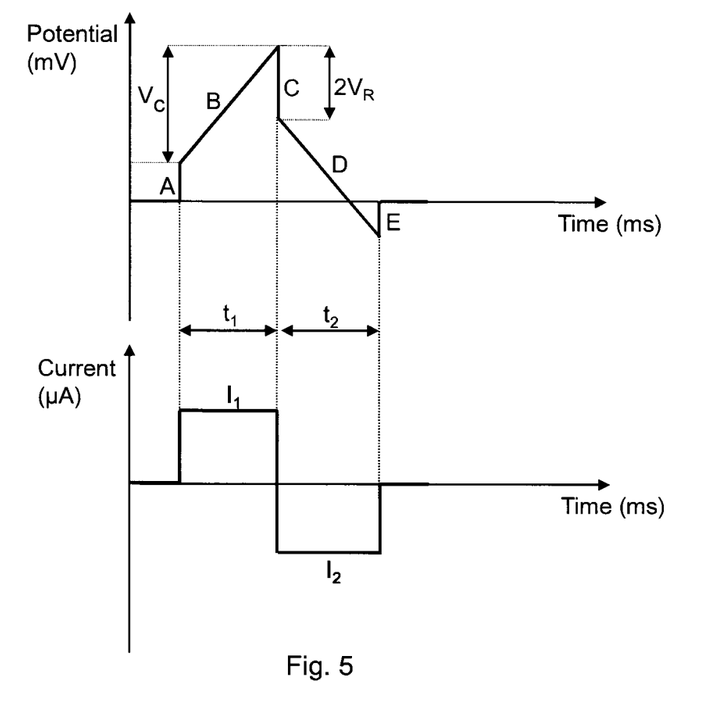
FIG. 5 shows a potential curve received in response to supply of constant currents during determined time periods to the sensor of the system in FIG. 1 according to a second embodiment of the method.

FIG. 4 and FIG. 5 show potential curves received by the potentials build up in response to supply of constant currents during determined time periods to the sensor of the system in FIG. 1 according to a first and a second embodiment, respectively, of the method. The constant currents, as square waves, are supplied from the current source 11 to the flow cell 12, i.e. the sensor.

In FIG. 4, a constant first current $I_1$ is supplied during a first time period $t_1$, a constant second current $I_2$ is supplied during a second time period $t_2$ and a constant third current is supplied during a third time period $t_3$ to the sensor. The second current $I_2$ has an opposite direction and has the same absolute value as the first current $I_1$. The second time period $t_2$ is equal to the first time period $t_1$ multiplied with a factor two. The third current $I_3$ has the same direction and the same absolute value as the first current $I_1$. The third time period $t_3$ is equal to said first time period $t_1$.

In FIG. 5, a constant first current $I_1$ is supplied during a first time period $t_1$ and a constant second current $I_2$ is supplied during a second time period $t_2$ to the sensor. The second current $I_2$ has an opposite direction compared to the first current $I_1$ and has the same absolute value as the first current $I_1$. The second time period $t_2$ is equal to the first time period $t_1$. In this second embodiment, the third time period is zero, hence the constant third current $I_3$ will not be emitted.

FIG. 4 and FIG. 5 illustrates the potential curves, when positive control potentials have been used for starting the current supplies. If a negative control potential is used, a negative current is emitted and thus the potential curve received will be reversed.

When a cycle including the time periods $t_1$, $t_2$ and $t_3$ have lapsed, the potential across the sensor should be zero. Otherwise, an error may have affected the system, which will be discussed below.

The operation of the system 10 is controlled by the software of the processor 14. A method of measuring the capacitance C of the sensor will be described below, with reference to FIG. 4 and FIG. 5.

Initially, a working electrode is arranged into the flow cell 12 of the system 10. The electrode is coated with an insulating layer having a ligand arranged thereto forming an affinity surface on the electrode, as described above.

Before injection of the analyte, a reference capacitance of said sensor has to be determined.

The processor 14 starts the method by emitting a control potential U via the D/A converter 16 to the control terminal 20 of the current source 11. Then, the current source 11 supplies a constant current I to the flow cell 12. The constant current I is positive, when the control potential U is positive, and the constant current I is negative if the control potential U is negative.

When a constant first current $I_1$ is supplied, a potential $V_R$ is built up across the resistor 31 of the flow cell 12, corresponding to part A in FIG. 4 and FIG. 5. $V_R$ is the product of the constant first current $I_1$ and the resistance R. Thereafter, the capacitor C is charged and a potential $V_C$ is built up across the capacitor, as illustrated by part B.

The potential V build up across the flow cell 12 is simultaneously sampled several hundred times by the processor 14 via the differential amplifier 13 and the A/D converter 15.

When a determined potential V has been reached and/or a determined time period $t_1$ has lapsed, the control potential U is reversed so that a constant second current $I_2$ of opposite direction to the first current $I_1$, is emitted by the current source 11. Said second current $I_2$ has the same absolute value as the first current $I_1$, which was supplied in the beginning of the cycle. The second current $I_2$ is supplied during a second time period $t_2$ that is equal to said first time period $t_1$ multiplied with a factor 2.

The result is that the potential $V_C$ across the capacitor instantly decreases due to the potential drop across the resistor 31 of the flow cell 12, as shown in part C. The potential drop is twice the size $2V_R$ compared to the potential rise $V_R$ of part A, since the current drops to zero and then is reversed to the negative value of said current $I_1$.

The capacitor 32 is discharged, shown in part D, with the same rate as it is charged during part B, since the inclinations of the potential curve of B and D are equal.

Since $t_2$ is equal to $t_1$ multiplied with a factor 2, the potential curve will drop to the determined potential V having a negative value, during charging the capacitor, shown in part F. The current supply is terminated by ceasing the output of the control potential U when $t_2$ has lapsed.

By changing the direction of the control potential U, a constant third current $I_3$ is supplied during a third time period $t_3$, which is equal to $t_1$. The potential $V_C$ across the capacitor instantly decreases due to the potential drop across the resistor 31 of the flow cell 12, as shown in part G. The potential drop is twice the size $2V_R$ compared to the potential rise $V_R$ of part A, since the current $I_2$ firstly drops to zero and then is reversed to the opposite direction.

The third current $I_3$ has the same direction and the same absolute value as the first current $I_1$, shown by part H in FIG. 5. The supply of the third current $I_3$ is terminated by ceasing the output of the control potential U when $t_3$ has lapsed, resulting in that the potential V across the flow cell 12 returns to zero, as shown in part I.

The method of measuring according to a second embodiment will now be described with reference to FIG. 5. The initialization of the method is equivalent to the one described in the context of FIG. 4.

When a determined potential V has been reached and/or a determined time period $t_1$ has lapsed, the control potential U is changed, so that a constant second current $I_2$, of opposite direction to the first current $I_1$, is emitted by the current source 11. Said second current $I_2$ has the same absolute value as the first current $I_1$, and is supplied during a time period $t_2$ that is equal to the time period $t_1$. This results in that the potential $V_C$ across the capacitor instantly decreases due to the potential drop across the resistor 31 of the flow cell 12, as shown in part C. The potential drop is twice the size $2V_R$ compared to the potential rise $V_R$ of part A, since the current $I_2$ firstly drops to zero and then is reversed to the negative value of the current $I_1$. The potential V, comprising the components $V_R$ and $V_C$, is sampled several hundred times by the processor 14 via the differential amplifier 13 and the A/D converter 15.

The capacitor 32 is discharged, shown in part D, with the same rate as it is charged during part B, since the inclinations of B and D are equal.

The current supply is terminated by ceasing the output of the control potential U when $t_2$ has lapsed, resulting in that the potential V across the flow cell 12 returns to zero, as shown in part E.

The current supply is terminated by ceasing the output of the control potential U when $t_2$ has lapsed, resulting in that the potential V across the flow cell 12 returns to zero, as shown in part E.

By running the system during one or several cycles of supply of constant currents before injection of the analyte, a reference capacitance of the flow-cell containing the electrolyte is determined. This measurements can be performed for example every second minute for controlling the stability of the system before starting the method with the analyte. The capacitance C of the flow cell 12, i.e. the sensor, is directly proportional to the potential built up across the capacitor and is calculated by means of the inclination of the potential curve of the parts B, D, F and H in FIG. 4, or by means of the inclination of the potential curve of the parts B and D in FIG. 5.

Thereafter the analyte is injected into the flowcell in such way that the analyte is slowly flowing over the electrode. The calculation of the capacitance received, e.g. the decrease in capacitance, is then calculated.

The potential V built up across the sensor, which includes the components $V_R$ and $V_C$, is simultaneously sampled and measured several hundred times via the differential amplifier 13 and the A/D converter 15, which is possible since a current source 20 is used for feeding. The sampling is performed a plurality of times during each period of current supply, such as about 100-1000 times per period. The entire operations described are controlled by the processor 14.

A cycle is repeated, for example by an interval of 20 ms (50 Hz) for synchronization with the line potential. A determined time period may optionally lapse without current supply, as shown in FIG. 5, until a new cycle is initiated. For example, the determined value of the potential V could be 50 mV, but could be set to any other optional value. The time period between consecutive cycles could be 10 ms, other time periods may be possible, such as about 10 to 100 ms.

The potential V, built up across the flow cell 12, is measured and sampled several hundred times during a measuring cycle, since a current source is used for feeding.

The capacitance C of the flow cell 12, i.e. the sensor, is directly proportional to the potential built up across the capacitor and is calculated by means of the inclination of the potential curve of the parts B, D, F and H in FIG. 4, or by means of the inclination of the potential curve of the parts B and D in FIG. 5. The linearity of the potential curve offers a great advantage in calculating the capacitance. A reliable measurement can be made, since the inclinations are obtained with high accuracy.

$$C \times U = I \times t \quad (1)$$

$$C = I \times t / U \quad (2)$$

wherein U is the potential built up (increase) during the time period t, I is the constant current applied through the sensor, and C is the capacitance of the sensor.

Since a reference value of the capacitance of the sensor has been determined before the analyte was injected, the change in capacitance when adding the analyte can be calculated. The change in capacitance is directly proportional to the concentration of the analyte injected, thus a measurement of the capacitance before and after the injection will give the concentration of the analyte in the solution.

Four values of the capacitance can be calculated from a single cycle according to the first embodiment, illustrated in FIG. 4. If the charging and discharging of the capacitor 32 differs from each other during said single cycle, i.e. if at least one of the inclinations of part B, D, F and H differs from the other ones, an error has occurred and the values have to be discarded.

According to the second embodiment, as shown in FIG. 5, two values are obtained of the capacitance from a single cycle. If the inclinations of part B and D differ from each other, an error has occurred and the values have to be discarded.

By discharging the capacitor on purpose, the potential across the sensor is applied for a limited time period, resulting in that the chemical bindings on the electrode surface of the sensor are less affected. Also, the sensitive biomolecules are subjected to a more gentle treatment during the measuring process, which is favorable for the affinity. By charging and then discharging the sensor during a determined period of time, the process is controlled. The sensor is left at the same potential after discharging as before the supply of the current.

The method offers a control function to assure that any component of the system is not affected by distortions from the surroundings. The potential $V_C$ across the capacitor 32 of the flow cell 12 is proportional to the inclination of the part B, received when supplying the constant first current $I_1$ to the flow cell 12, and to the inclination of part D, when supplying the second current $I_2$ of opposite direction. If these inclinations differs in any way during a single cycle, it is an indication of that an error has affected the system. Referring to FIG. 5, the inclinations of B, D, F and H should be equal; otherwise an error has affected the system.

The potential $V_R$ across the resistance 31 of the flow cell 12 is proportional to the heights of parts A, C, E, G and I. According to the first embodiment, part A and I should be of equal height and part C and G should be twice that height. If this is not the case, some error of the system or some disturbance is affecting the system. Referring to FIG. 5, part A and E should be of equal height, and part C and G should be twice those heights.

The measurement of the capacitive change is not affected by the quality of the flow cell 12. It is only regarded as a resistance R when the method is initiated by applying the control potential U, since the capacitor C at this moment is not charged. This means that the starting point at the horizontal axis can be chosen irrespective of where the measurements start, and will not affect the measurements.

The resistance R, which is not involved for the calculation of the capacitance C according to the inventive method, can be used as an identification of an electrode of a sensor. Every biosensor electrode is unique, and the variations in quality between different sensor electrodes are related to the resistance R, which gives a unique feature that can be used as a protection for copying. A one-time writeable chip may be arranged at each sensor electrode. The chip is communicating with the components of the system and may verify its identity for performing measurements by a determined biosensor electrode. If the chip is copied and arranged to another sensor electrode, it is not possible to unlock the measuring process, since the sensor electrode is not the determined one. For example, a reference curve of the capacitance C can be saved in the chip, and then be used for calibration against calculated values of C. This reference curve can be coded by a control key, based on the specific differences in capacitance C; thereafter it is not possible to program the chip once more.

Existing devices for measurement of the capacitance of biosensors are based on potential supply to the flow cell, and the current response thereto will be the base for calculating. Potential feed is sensitive for external electronic disturbances, which will affect the background noise. Capacitive measurements, based on potential supply, have shown an underlying variability of about 1 nanofarad.

The method according to the invention is based on supply of a constant current supply, which has shown will lead to a decrease in electronic noise compared to supply of a potential. Also, the background variability has diminished, experimental trials has shown about 100 picofarad, i.e. has diminished by 90% compared to prior art methods, see the tables below.

Example

Sensitivity Analysis

1. Prior Art System
Cholera Concentration 1

| C (nF) | Delta (nF) | standard deviation |
|---|---|---|
| 236.35 | | |
| 235.96 | 0.39 | |
| 236.11 | −0.15 | |
| 236.55 | −0.44 | |
| 235.75 | 0.8 | |
| 235.85 | −0.1 | 0.306447 |

2. Prior Art System
Cholera Concentration 2

| C (nF) | Delta (nF) | standard deviation |
|---|---|---|
| 255.37 | | |
| 256.41 | 1.04 | |
| 255.67 | −0.74 | |
| 255.74 | 0.07 | |
| 256.76 | 1.02 | |
| 255.49 | −1.27 | 0.552618 |

3. Inventive System
Cholera Concentration 3

| C (nF) | Delta (nF) | standard deviation |
|---|---|---|
| 147.078 | | |
| 147.067 | 0.011 | |
| 147.054 | 0.013 | |
| 147.052 | 0.002 | |
| 147.031 | 0.021 | |
| 147.06 | −0.029 | 0.015875 |

Several advantages for measuring the capacitance, by using electrochemical principles, are achieved by the inventive method compared to existing measuring methods within the biochemical field.

The invention contributes to achieve reliable and accurate values of the capacitance, which can be used for different applications. Examples of such applications are determination of concentrations of specific agents present in any type of fluid, specifically by using a suitable ligand for determination of an interaction with the corresponding analyte. Determination of the binding events using the invention could utilize systems based on antibodies and antigens, lectins and sugar moieties or other affinity partner molecules.

The sensitivity of any capacitive biosensor is very high; hence it is desirable to measure the capacitance with a high resolution and accuracy, which is achieved by the inventive method. Said method is stable, since the constant current to the sensor is not interacting with line potentials.

The supply of the constant current of a couple of microamperes is more favourable for the electrodes and the biorecognition surface. The electrode is not worn out, and the ligand is not consumed as fast as when a potential pulse is applied according to existing methods.

The affinity surface is less affected, since the charging and discharging of the sensor are performed in a controlled way due to the constant current, which is applied during determined time periods and selected directions in relation to each other.

The linearity of the potential curve, received in response to the supply of the constant current, offers a simple and accurate way for calculating the capacitance, since this is proportional to the inclination of said curve.

The resistance of the sensor, and hence the quality of the electrode, is irrelevant for the calculation of the capacitance. The benefits of the inventive method are obvious in comparison to existing methods and devices, wherein the resistance firstly has to be calculated and thereafter the capacitance is determined by a logarithmic equation; the different steps will all contribute to a higher inaccuracy of the capacitance measurements.

By the inventive method, two or more values of the capacitance are received for each single measuring cycle, which in many aspects contribute to a higher accuracy. All calculated values can be used for calculating the capacitance change, while simultaneously a validity control is performed, since all values within the same cycle have to correspond. When a preset amount of values are necessary for a safe result, this will be achieved within a shorter time period compared to existing methods.

Also from a cost effective aspect, the inventive method offers a less expensive way for performing measurements, since the ligand and the electrode can be used for a longer time period in combination with more values for calculating the capacitance, thus extending the intervals for exchanging or manually regenerating the working electrode.

The potential across the resistance $V_R$ of the sensor, received from the potential curve, may also be utilised for controlling the reliability and accuracy of the method. If $V_R$ does not return to zero, when a cycle has lapsed, an error is affecting the system and the corresponding values of the potentials built up across the capacitor $V_C$ have to be discarded.

Rising demands with regard to characterization of low levels of impurities show a need for development of high-sensitivity analytical techniques that are relatively fast, convenient to use, and possible to integrate in the production process for on-line measurements. Impurities are typically present in minute amounts. It is necessary that the analytical procedures are adapted for detection and quantification of extremely low concentrations of the target molecules. Also, it is important to analyse samples as rapidly as possible and preferably in real time, so that it will be possible to change conditions quickly in order to react to observed increases in the concentration of key impurities.

The inventive method is addressing these demands. The method is well suited for the detection of exceedingly low levels of bacterial toxins and viral contaminants present in the sample, as well as for tracking doping substances in blood or for detecting biological markers for viral diseases, e.g. HIV. The method can be used for the detection of unknown molecules in a solution, and for the detection of residuals of agents that remain in pharmaceutical preparations.

Hence, in a second aspect, the invention relates to a use of the method for detection and quantification of an interaction between a ligand and an analyte, for example, the use can be applied when the ligand is an antibody and the analyte is an antigen.

Also, the use of the method can be applied to any analyte being a biomolecule and its either natural or synthetic binding ligand.

Also, the use of the method may be applied for detecting an interaction between an analyte and a ligand, wherein the ligand and the analyte form an affinity pair of any of a couple selected from the list:

lectin—glycoconjugate,
lectin—carbohydrate,
protein with selective binding to other proteins, e.g. protein A and immunoglobulin A,
receptor—receptor binding entity,
nucleic acid—nucleic acid with complementary base sequence,
enzyme—enzyme inhibitor
peptide from phage library and its target molecule;

Any of the two parts of the affinity pair might be the ligand and the other part might be the analyte.

Another example of the use of the method for detecting an interaction is when the ligand is a sugar-binding protein (lectin) and the analyte is a glycoprotein.

Still another use of the method is when the ligand is a sugar-binding protein (lectin) and the analyte is a cell-surface structure.

Yet another use of the method is when the ligand is a membrane-bound receptor and the analyte is the corresponding binding partner.

In the claims, the term "comprise/comprising" does not exclude the presence of other elements or steps. Furthermore, although individually listed, a plurality of means, elements or method steps may be implemented. Reference signs in the claims are provided as a clarifying example and shall not be construed as limiting the scope in any way.

The invention claimed is:

1. A method of measuring a capacitance (C) of a sensor having the capacitance and a resistance, the sensor including a working electrode that is coated by an insulating layer with a ligand arranged thereto forming an affinity surface on said electrode, the method comprising the steps of:
    bringing said electrode into contact with an analyte;
    supplying a constant first current ($I_1$) to the sensor during a first time period ($t_1$) by means of a current source until a potential built up across the sensor has reached a predetermined value (V), and
    simultaneously sampling the potential (V) built up across the sensor;
    supplying a constant second current ($I_2$) to the sensor during a second time period ($t_2$) by means of the current source, the second current ($I_2$) having an opposite direction compared to the first current ($I_1$) and having a same absolute value as the first current ($I_1$), wherein the second time period ($t_2$) is equal to said first time period ($t_1$) or is equal to said first time period ($t_1$) multiplied with a factor two, and
    simultaneously sampling the potential (V) built up across the sensor;
    supplying a constant third current ($I_3$) to the sensor during a third time period ($t_3$) by means of the current source, the third current ($I_3$) having the same direction as the first current ($I_1$) and having the same absolute value as the first current ($I_1$), wherein if said second time period ($t_2$) is equal to said first time period ($t_1$), the third time period ($t_3$) is zero, and if said second time period ($t_2$) is equal to said first time period ($t_1$) multiplied with a factor two, the third time period ($t_3$) is equal to said first time period ($t_1$), and
    simultaneously sampling the potential (V) built up across the sensor; and
    calculating the capacitance (C) of the sensor by means of an inclination (B, D, F, H) of a potential curve received by the potential (V) built up across the sensor in response to the supply of the constant currents ($I_1$, $I_2$, $I_3$), if said potential (V) has returned to zero when a cycle including said time periods ($t_1$, $t_2$, $t_3$) has lapsed.

2. The method according to claim 1, wherein said capacitance (C) is discarded if the potential (V) built up across the sensor does not return to zero when the third time period ($t_3$) has lapsed.

3. The method according to claim 1, wherein said sampling is performed a plurality of times during each time period ($t_1$, $t_2$, $t_3$) of current supply.

4. The method according to claim 1, wherein if at least one inclination (B, H, F, H) of said potential curve differs from the other ones, an error has occurred and the capacitance calculated has to be discarded.

5. The method according to claim 1, wherein the resistance of the electrode is determined from a vertical part (A, C, G, E, I) of said potential curve, and if said resistance is altered after consecutive supplies of the constant currents ($I_1$, $I_2$, $I_3$), the corresponding capacitance (C) calculated is discarded.

6. The method according to claim 5, wherein said resistance is used for identification of the electrode.

7. The method according to claim 1, is used for detection and quantification of an interaction between a ligand and an analyte.

8. The method according to claim 7, wherein said capacitance is discarded if the potential built up across the sensor does not return to zero when the third time period has lapsed.

9. The method according to claim 7, wherein said sampling is performed a plurality of times during each time period of current supply.

10. The method according to claim 7, wherein if at least one inclination of said potential curve differs from the other ones, an error has occurred and the capacitance calculated has to be discarded.

11. The method according to claim 7, wherein the resistance of the electrode is determined from a vertical part of said potential curve, and if said resistance is altered after consecutive supplies of the constant currents the corresponding capacitance calculated is discarded.

12. The method according to claim 11, wherein said resistance is used for identification of the electrode.

13. The method according to claim 7, wherein the ligand is an antibody and the analyte is an antigen.

14. The method according to claim 7, wherein the ligand and the analyte form an affinity pair of any of a couple selected from:
lectin—glycoconjugate,
lectin—carbohydrate,
protein with selective binding to other proteins, e.g. protein A and immunoglobulin A,
receptor—receptor binding entity,
nucleic acid—nucleic acid with complementary base sequence,
enzyme—enzyme inhibitor,
peptide from phage library—its target molecule;
wherein any of the two parts of the affinity pair might be the ligand and the other part might be the analyte.

15. The method according to claim 7, wherein the analyte is any biomolecule and the ligand is a natural or synthetic corresponding binding partner to said any biomolecule.

* * * * *